US007649119B2

(12) United States Patent
Teles et al.

(10) Patent No.: US 7,649,119 B2
(45) Date of Patent: Jan. 19, 2010

(54) METHOD FOR THE PRODUCTION OF CYCLIC KETONES

(75) Inventors: Joaquim Henrique Teles, Otterstadt (DE); Beatrice Rößler, Weisenhaim Am Sand (DE); Rolf Pinkos, Bad Dürkheim (DE); Gerd Tebben, Mannheim (DE); Christian Müller, Mannheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 12/306,841

(22) PCT Filed: Jun. 27, 2007

(86) PCT No.: PCT/EP2007/056396

§ 371 (c)(1),
(2), (4) Date: Dec. 29, 2008

(87) PCT Pub. No.: WO2008/000757

PCT Pub. Date: Jan. 3, 2008

(65) Prior Publication Data

US 2009/0281357 A1 Nov. 12, 2009

(30) Foreign Application Priority Data

Jun. 29, 2006 (EP) .................................. 06116261

(51) Int. Cl.
*C07C 45/27* (2006.01)
(52) U.S. Cl. ...................................... 568/363
(58) Field of Classification Search ................. 568/363
See application file for complete search history.

(56) References Cited

U.S. PATENT DOCUMENTS

| 316,917 | A | | 4/1885 | Russell |
| 2,636,898 | A | * | 4/1953 | Buckley ..................... 560/101 |
| 3,804,914 | A | | 4/1974 | Fahey |
| 4,985,572 | A | | 1/1991 | Kitson et al. |
| 5,128,296 | A | | 7/1992 | Matson et al. |
| 5,177,278 | A | | 1/1993 | Sanchez |
| 5,180,870 | A | | 1/1993 | Paciello |
| 5,210,349 | A | | 5/1993 | Matson et al. |
| 5,321,176 | A | * | 6/1994 | Sanchez ..................... 585/277 |
| 7,105,704 | B2 | | 9/2006 | Panov et al. |
| 7,153,114 | B2 | | 12/2006 | Snyder et al. |
| 7,282,612 | B2 | | 10/2007 | Panov et al. |
| 7,449,606 | B2 | | 11/2008 | Teles et al. |
| 2005/0203316 | A1 | | 9/2005 | Panov et al. |
| 2006/0106258 | A1 | | 5/2006 | Panov et al. |
| 2008/0255393 | A1 | | 10/2008 | Teles et al. |
| 2008/0275276 | A1 | | 11/2008 | Teles et al. |

FOREIGN PATENT DOCUMENTS

| DE | 25 19 817-OS | 11/1976 |
| DE | 2519817 A1 | 11/1976 |
| DE | 10 2004 046 167 | 4/2006 |
| DE | 102004046167 A1 | 4/2006 |
| EP | 0 285 420 A1 | 10/1988 |
| EP | 0285420 A1 | 10/1988 |
| EP | 1 477 219 A1 | 11/2004 |
| EP | 1477219 A1 | 11/2004 |
| GB | 649680 | 1/1951 |
| GB | 1551741 | 8/1979 |
| SU | 1133257 A | 1/1985 |
| WO | WO-03/078370 A1 | 9/2003 |
| WO | WO-03/078371 A1 | 9/2003 |
| WO | WO-03/078372 A1 | 9/2003 |
| WO | WO-03/078374 A1 | 9/2003 |
| WO | WO-03/078375 A1 | 9/2003 |
| WO | WO-2004/000777 A1 | 12/2003 |
| WO | WO-2005/030689 A2 | 4/2005 |
| WO | WO-2005/030690 A2 | 4/2005 |

OTHER PUBLICATIONS

U.S. Appl. No. 12/306,827, filed Dec. 29, 2008.
U.S. Appl. No. 12/306,807, filed Dec. 29, 2008.
U.S. Appl. No. 12/306,815, filed Dec. 29, 2008.
Schiffer, Thomas, et al., "Cyclodoecanol, Cyclododecanone, and Laurotactam" Wiley-VCH Verlag GmbH & Co. KGaA, Weinheim, pp. 1-5, (2005).
Schiffer, Thomas, et al, "Cyclododecatriene, Cyclooctadiene, and 4-Vinylcyclohexene" Wiley-VCH GmbH & Co. KGaA, Weinheim, pp. 1-4, (2005).
Weber, H., et al., " Zur Bildungsweise Von cis, trans, trans-Cyclododecatrien-(1.5.9) Mittel Titanhaltiger Ziegler-Katalysatoren" Herrn Prof. Dr. Clemens Schopf zum 65. Geburtstag gewidmet, pp. 10-20, Mar. 11, 1964.
Fahey, Daryl R., "Selective Hydrogenation of 1,5,9-Cyclododecatriene to Cyclododecene Catalyzed by Ruthenium Complexes" The Journal of Organic Chemistry, vol. 38, No. 1, pp. 80-87 (1973).

(Continued)

*Primary Examiner*—Sikarl A Witherspoon
(74) *Attorney, Agent, or Firm*—Connolly Bove Lodge & Hutz LLP

(57) ABSTRACT

The present invention relates to a process for preparing a cyclic ketone having from 7 to 16 carbon atoms, which comprises at least the steps (a) oxidation of a composition (I) comprising at least one cyclic olefin which has from 7 to 16 carbon atoms and at least one C—C double bond by means of dinitrogen monoxide to give a composition (A),
(b) treatment of the composition (A) with at least one base to give a composition (B).

16 Claims, No Drawings

OTHER PUBLICATIONS

Panov, Gennady I., et al., "Non-Catalytic Liquid Phase Oxidation Of Alkenes With Nitrous Oxide. I. Oxidation Of Cyclohexene To Cyclohexanone" React.Kinet.Catal.Lett., vol. 76, No. 2, pp. 401-402, (2002).

Dubkov, Konstantin A., et al., "Non-Catalytic Liquid Phase Oxidation of Alkenes With Nirtous Oxide. 2. Oxidation Of Cyclopentene To Cyclopentanone." React.Kinet.Catal.Lett., vol. 77, No. 1, pp. 197-205, (2002).

Starokon, E.V., et al., "Liquid Phase Oxidation of Alkenes with Nitrous Oxide to Carbonyl Compounds" Adv. Synth. Catal., vol. 346, pp. 268-274, (2004).

Falkovich, M.I., "Cyclo:decanone sepn. from cyclodecane oxidn. prods.—by treatment with alkali and water. sepn. of aq. and organic phase, rectification and dehydrogenation" p. 638, (Jul. 1, 1985).

* cited by examiner

METHOD FOR THE PRODUCTION OF CYCLIC KETONES

CROSS-REFERENCE TO RELATED APPLICATIONS

This application is a national stage application (under 35 U.S.C. § 371) of PCT/EP2007/056396, filed Jun. 27, 2007, which claims benefit of European application 06116261.6, filed Jun. 29, 2006.

BACKGROUND OF THE INVENTION

The present invention relates to a process for preparing a cyclic ketone having from 7 to 16 carbon atoms, which comprises at least the oxidation of a composition (I) comprising at least one cyclic olefin which has from 7 to 16 carbon atoms and at least one C—C double bond by means of dinitrogen monoxide to give a composition (A) and treatment of the composition (A) with at least one base to give a composition (B).

The oxidation of an olefinic compound by means of dinitrogen monoxide to form an aldehyde or a ketone is described, for example, in GB 649,680 or the equivalent U.S. Pat. No. 2,636,898. In both documents, it is disclosed in general terms that the oxidation can in principle be carried out in the presence of a suitable oxidation catalyst.

The more recent scientific articles by G. I. Panov et al., "Non-Catalytic Liquid Phase Oxidation of Olefins with Nitrous Oxide. 1. Oxidation of Cyclohexene to Cyclohexanone", React. Kinet. Catal. Lett. Vol. 76, No. 2 (2002) pp. 401-405, and K. A. Dubkov et al., "Non-Catalytic Liquid Phase Oxidation of Olefins with Nitrous Oxide. 2. Oxidation of Cyclopentene to Cyclopentanone", React. Kinet. Catal. Lett. Vol. 77, No. 1 (2002) pp. 197-205, likewise describe oxidations of olefinic compounds by means of dinitrogen monoxide. A scientific article "Liquid Phase Oxidation of Olefins with Nitrous Oxide to Carbonyl Compounds" by E. V. Starokon et al. in Adv. Synth. Catal. 2004, 346, 268-274, also reports a mechanistic study of the oxidation of olefins by means of dinitrogen monoxide in the liquid phase.

The synthesis of carbonyl compounds from olefins using dinitrogen monoxide is also described in various international patent applications. Thus, WO 03/078370 discloses a process for preparing carbonyl compounds from aliphatic olefins using dinitrogen monoxide. The reaction is carried out at temperatures in the range from 20 to 350° C. and pressures of from 0.01 to 100 atm. WO 03/078374 discloses a corresponding process for preparing cyclohexanone. According to WO 03/078372, cyclic ketones having from 4 to 5 carbon atoms are prepared. According to WO 03/078375, cyclic ketones are prepared from cyclic olefins having from 7 to 20 carbon atoms under these process conditions. WO 03/078371 discloses a process for preparing substituted ketones from substituted olefins. WO 04/000777 discloses a process for reacting diolefins and polyolefins with dinitrogen monoxide to form the corresponding carbonyl compounds.

WO 2005/030690 and WO 2005/030689 describe processes for preparing cyclododecanone, in which an oxidation by means of dinitrogen monoxide is carried out in one process step. WO 2005/030690 describes a process for preparing cyclododecanone by oxidation of 1,5,9-cyclododecatriene (CDT) by means of $N_2O$ to form cyclododeca-4,8-dienone and subsequent hydrogenation of cyclododeca-4,8-dienone to give cyclododecanone.

In all processes, the purity of the crude products without addition of purification is not sufficient for some applications. Organic compounds having oxygen-comprising groups, in particular, are frequently still comprised in the products obtained in excessively large amounts.

In the oxidation of olefins by means of dinitrogen monoxide, it is possible for, for example, aldehydes to be formed as by-products, as described, for example, in Panov et al., Adv. Synth. Catal. (2004) 346, 268-274.

This is problematical insofar as cyclic ketones are required in high purity for various applications. Thus, for example, cyclododecanone is an important intermediate in the preparation of, for example, laurolactam, dodecanedicarboxylic acid and polyamides derived therefrom, for example Nylon 12 or Nylon 6.12. The impurities such as aldehydes comprised in the cyclic ketones can be removed only with difficulty by conventional purification methods such as distillation, extraction or recrystallization, since the functional groups and the number of carbon atoms are similar. For this reason, a very complicated purification, for example by multistage distillation or crystallization, is necessary in these cases. These purification methods are therefore complicated and costly.

BRIEF SUMMARY OF THE INVENTION

It was therefore an object of the present invention to provide a process by means of which cyclic ketones can be obtained in high purity in a simple manner and at low cost.

According to the invention, this object is achieved by a process for preparing a cyclic ketone having from 7 to 16 carbon atoms, which comprises at least the steps (a) oxidation of a composition (I) comprising at least one cyclic olefin which has from 7 to 16 carbon atoms and at least one C—C double bond by means of dinitrogen monoxide to give a composition (A), (b) treatment of the composition (A) with at least one base to give a composition (B).

It has surprisingly been found that, in particular, a mixture of cyclic ketones with by-products such as cyclic and open-chain aldehydes having an identical or similar number of carbon atoms can be selectively depleted in the by-products by firstly treating the mixture with a base, for example with a base at elevated temperature. For the purposes of the present invention, the term "depleted" means that the ratio of aldehyde to cyclic ketone is reduced and, in particular, the cyclic ketone is essentially not attacked.

DETAILED DESCRIPTION OF THE INVENTION

For the purposes of the present patent application, the term "treatment" refers to contacting of a composition with at least one base.

The process of the invention enables cyclic ketones having a purity of, for example, >99.5% to be obtained. The process of the invention can easily be combined with existing plants, so that no costly modifications are necessary. Furthermore, the process of the invention makes it possible to improve the yield of cyclic ketones on oxidation of olefins with dinitrogen monoxide since the treatment with base is generally very selective and less product is therefore lost.

The reaction in step (a) can generally be carried out using all procedures in which the olefin and dinitrogen monoxide react with one another.

In step (a) of the process of the invention, the cyclic olefin is oxidized by reaction with dinitrogen monoxide. It is possible to use at least one suitable solvent or diluent for the reaction of the cyclic olefin with dinitrogen monoxide. Such solvents or diluents are, inter alia, cyclic alkanes, for example cyclododecane, or cyclododecanone or saturated aliphatic or aromatic, optionally alkyl-substituted hydrocarbons. Essentially all customary solvents and/or diluents are suitable, provided that they have neither a C—C double bond nor a C—C triple bond nor an aldehyde group.

In general, the addition of a solvent or diluent is not necessary in the reaction of the cyclic olefin with dinitrogen monoxide.

The temperatures in the reaction of the cyclic olefin with dinitrogen monoxide are preferably in the range from 140 to 350° C., more preferably in the range from 180 to 320° C. and particularly preferably in the range from 200 to 300° C.

It is possible to carry out the reaction of the cyclic olefin with dinitrogen monoxide at two or more temperatures or in two or more temperature ranges which are each within the abovementioned limits. Temperature changes during the course of the reaction can be carried out continuously or discontinuously.

The pressures in the reaction of the cyclic olefin with dinitrogen monoxide are preferably above the autogenous pressure of the starting material or product mixture at the selected reaction temperature or the selected reaction temperatures. The pressures are preferably in the range from 1 to 1000 bar, more preferably in the range from 40 to 300 bar and particularly preferably in the range from 50 to 200 bar.

The pressure in the reaction vessel, preferably in a least one tube reactor, is generally greater than or equal to, preferably greater than, the autogenous pressure of the starting material mixture or the product mixture at the selected reaction temperature or the selected reaction temperatures in the reaction vessel. In general, the reaction pressures are in the range from 1 to 14 000 bar, preferably in the range from the autogenous pressure to 3000 bar, particularly preferably in the range from the autogenous pressure to 1000 bar and very particularly preferably in the range from the autogenous pressure to 325 bar, for example from 50 to 200 bar.

It is possible to carry out the reaction of the cyclic olefin with dinitrogen monoxide at two or more pressures or in two or more pressure ranges which are each within the abovementioned limits. Pressure changes during the course of the reaction can be carried out continuously or discontinuously.

The reactors which can be used for the reaction of the cyclic olefin with dinitrogen monoxide are not subject to any particular restrictions. In particular, the reaction can be carried out batchwise or continuously. Accordingly, it is possible to use, for example, at least one CSTR (continuous stirred tank reactor) having at least one internal and/or at least one external heat exchanger, at least one tube reactor, at least one shell-and-tube reactor or at least one loop reactor as reactors. It is likewise possible to configure at least one of these reactors so that it has at least two different zones. Such zones can differ, for example, in terms of reaction conditions such as the temperature or the pressure and/or in terms of the geometry of the zone, for example the volume or cross section. If the reaction is carried out in two or more reactors, it is possible to use two or more identical types of reactor or at least two different types of reactor.

The reaction of the cyclic olefin with dinitrogen monoxide is preferably carried out in a single reactor. For example, preference is given to a continuous reaction.

The residence time of the reaction mixture in the at least one reactor in the reaction of the cyclic olefin with dinitrogen monoxide is generally in the range up to 20 hours, preferably in the range from 0.1 to 20 hours, more preferably in the range from 0.2 to 15 hours and particularly preferably in the range from 0.25 to 10 hours.

In the feed supplied to the reaction of dinitrogen monoxide with the cyclic olefin, the molar ratio of dinitrogen monoxide to the cyclic olefin is generally in the range from 0.05 to 4, preferably in the range from 0.06 to 1, more preferably in the range from 0.07 to 0.5 and particularly preferably in the range from 0.1 to 0.4.

The reaction of the cyclic olefin with dinitrogen monoxide can be carried out so that a conversion of the cyclic olefin in the range up to 50%, preferably in the range from 5 to 30% and particularly preferably in the range from 10 to 20%, is achieved at a very high selectivity to the cyclic ketone. The selectivity, based on the cyclic ketone, is generally at least 90%, preferably at least 92.5% and particularly preferably at least 93%.

According to the invention, it is in principle possible to react any cyclic olefin having from 7 to 16 carbon atoms or any mixture of two or more different cyclic olefins having from 7 to 16 carbon atoms with dinitrogen monoxide. Suitable olefins are, for example, cyclic olefins having one or more C—C double bonds. Further preference is given to cyclic olefins having one or more C—C double bonds, for example cycloheptene, cyclooctene, cyclodecene, cycloundecene, cyclododecene, 1,5-cyclooctadiene, 1,5-cyclododecadiene or 1,5,9-cyclododecatriene.

Particular preference is given to using cyclododecene or 1,5,9-cyclododecatriene as olefin. Mention may here be made of, for example, 1,5,9-cyclododecatrienes, for example cis,trans,trans-1,5,9-cyclododecatriene or cis,cis,trans-1,5,9-cyclododeca-triene or all-trans-1,5,9-cyclododecatriene.

Preference is given to using cis,trans,trans-1,5,9-cyclododecatriene as cyclododeca-triene.

In a preferred embodiment, the present invention therefore provides a process for preparing a ketone as described above, wherein the olefin is selected from the group consisting of cyclododecene and cyclododecatriene, in particular 1,5,9-cyclododeca-triene.

The reaction of the cyclic olefin with dinitrogen monoxide can in principle be carried out in the presence of a catalyst, but also without addition of a catalyst.

For the purposes of the present invention, dinitrogen monoxide can be used in pure form or in the form of a gas mixture comprising dinitrogen monoxide.

It is in principle possible to use any gas mixture comprising dinitrogen monoxide in step (a) of the process of the invention. It is also possible, according to the invention, to purify or concentrate the gas mixture comprising dinitrogen monoxide before it is used in the reaction in step (a). A suitable purification method comprises, for example, absorption of the gas mixture in an organic solvent or water, desorption of the gas mixture from the laden organic solvent or the laden water and setting of the content of nitrogen oxides $NO_x$ in the gas mixture to not more than from 0.01 to 0.001% by volume, based on the total volume of the gas mixture. Such a process is described, for example, in DE 10 2004 046 167.8, whose relevant contents are fully incorporated by reference into the present patent application.

The gas mixture comprising dinitrogen monoxide which is used can in principle originate from any source. In particular, it is possible to use the offgas of a process as described in DE 10 2004 046 167.8 as dinitrogen monoxide source.

The term "gas mixture" as used in the context of the present invention refers to a mixture of two or more compounds which are in the gaseous state at ambient pressure and ambient temperature. At a different temperature or different pressure, the gas mixture can also be in another state of matter, for example liquid, and will for the purposes of the present invention continue to be referred to as gas mixture.

According to the invention, it is possible to use a mixture of various offgases.

In a further preferred embodiment of the present invention, the at least one offgas comprising dinitrogen monoxide originates from an adipic acid plant, a dodecanedioic acid plant, a hydroxylamine plant and/or a nitric acid plant, with the latter in turn preferably being operated using an offgas from an adipic acid plant, a dodecanedioic acid plant or a hydroxylamine plant.

According to the invention, the gas mixture can be used in gaseous form. However, it is also possible firstly to treat the gas mixture comprising dinitrogen monoxide so that the gas mixture is present in liquid or supercritical form and then use it. The gas mixture or dinitrogen monoxide can be liquefied by appropriate choice of the pressure or temperature. It is likewise possible, for the purposes of the present invention, to dissolve the gas mixture in a solvent.

According to the invention, the composition (I) usually comprises the cyclic olefin in an amount of more than 80% by weight, preferably from 85 to 99.999% by weight, in particular from 90 to 99.99% by weight, particularly preferably from 92 to 99.9% by weight, for example from 95 to 99.8% by weight. The composition (I) can usually comprise further compounds, in particular organic compounds, in addition to the cyclic olefin.

The composition (I) can comprise, for example, vinylcyclohexene, cyclooctadiene and, for example, bicyclic isomers of 1,5,9-cyclododecatriene as organic compounds. It is also possible for traces of $C_{16}$ components, $C_{24}$ components or higher oligomers to be comprised.

In the reaction in step (a) of the process of the invention, the cyclic olefin comprised in the composition (I) is oxidized by means of dinitrogen monoxide. This gives a composition (A) comprising at least one cyclic ketone.

The composition (A) in the process of the present invention comprises at least one cyclic ketone having from 7 to 16 carbon atoms. According to the invention, the composition (A) comprises the cyclic ketone in an amount of more than 5% by weight, preferably more than 10% by weight, more preferably from 10 to 90% by weight, in particular from 11 to 50% by weight, particularly preferably from 12 to 40% by weight, very particularly preferably from 13 to 30% by weight, for example from 14 to 20% by weight or from 15 to 18% by weight. The composition (A) usually comprises further compounds, in particular organic compounds, for example unreacted starting material or organic compounds having oxygen-comprising groups, for example alcohols, aldehydes or epoxides, in addition to the cyclic olefin. Here, the organic compounds can have, in particular, the same number of carbon atoms as the cyclic ketone comprised in the composition (A).

The composition (A) can be used directly in step (b) of the process of the invention. However, it is also possible to subject the composition (A) to an intermediate treatment before step (b). For example, unreacted starting material can be separated off from the composition (A). It is likewise possible for by-products of the oxidation, for example diketones, to be separated off. According to the invention, unreacted starting material and diketones can preferably be separated off. The separation can, for example, be carried out by distillation in one or more columns, preferably in at least two columns.

According to the invention, the composition (A) is treated with at least one base in step (b). The process conditions for the treatment can be varied within a wide range, as long as it is ensured that the concentration of at least one interfering secondary component, in particular at least one aldehyde is reduced.

According to the invention, the amount of the aldehyde is reduced in this treatment while the cyclic ketone is essentially not attached. Here, open-chain aldehydes are, according to the invention, preferably degraded to an extent of more than 90%, in particular more than 95% and particularly preferably 99.99%. Cyclic aldehydes having an exocyclic aldehyde group are preferably degraded to an extent of up to 30%, in particular up to 35% and particularly preferably up to 40%. According to the invention, the cyclic ketone is degraded only to an extent of from 0.5 to 2.0%, preferably from 0.75 to 1.75%, in particular from 1.0 to 1.5%.

In general, the treatment with base is continued until at least 90%, preferably at least 95%, of the interfering secondary component, in particular the at least one aldehyde, preferably the at least one open-chain aldehyde, have been reacted.

According to the invention, the treatment with at least one base in step (b) is preferably carried out for a period of from 1 minute to 10 hours, in particular from 5 minutes to 5 hours, particularly preferably from 10 to 60 minutes, more preferably from 20 to 50 minutes.

The treatment in the process of the invention can, in particular, be carried out at a temperature of from 100 to 250° C., preferably from 110 to 220° C., particularly preferably from 120 to 200° C., more preferably from 150 to 190° C.

In a further embodiment, the present invention therefore also provides a process as described above for preparing a cyclic ketone having from 7 to 16 carbon atoms, wherein the treatment in step (b) is carried out at a temperature of from 100 to 250° C. for a period of from 1 minute to 10 hours.

All possible types of reactor are suitable for the treatment with the base. For a continuous reaction, preference is given to using reactors having tube characteristics, e.g. tube reactors, cascades of stirred vessels or comparable reactors. For a discontinuous process (batch process), simple stirred vessels are well suited. The reaction preferably proceeds essentially homogeneously in the liquid phase.

The treatment in step (b) preferably comprises two substeps (b1) and (b2), with the composition (A) being treated with at least one base in step (b1) and the base being separated off in step (b2).

In a further embodiment, the present invention therefore also provides a process as described above for preparing a cyclic ketone having from 7 to 16 carbon atoms, wherein the step (b) comprises the substeps (b1) and (b2):

(b1) treatment of the composition (A) with at least one base (b2) removal of the base.

The removal of the base in (b2) can be carried out by all customary methods, for example by distillation. Particularly when NaOH or KOH is used as base, the removal is preferably effected by evaporation, for example in the form of a falling film evaporator, a wiped film evaporator or a helical tube evaporator, or by extraction of the base, for example with water.

For the purposes of the present invention, it is in principle possible to use all suitable bases. Preference is given to using organic or inorganic bases whose conjugate acid has a $pK_a$ relative to water of >9. For the purposes of the present invention, preference is given to, for example, trialkylamines, alkali metal alkoxides of alkaline earth metal alkoxides and tetraalkylammonium, alkali metal or alkaline earth metal hydroxides. Very particular preference is given to sodium hydroxide and potassium hydroxide.

In a further embodiment, the present invention therefore also provides a process as described above for preparing a cyclic ketone having from 7 to 16 carbon atoms, wherein the base is selected from among sodium hydroxide and potassium hydroxide.

The base can, according to the invention, be used either as a pure substance or as a solution. Liquid bases are preferably used without addition of a solvent. Solid bases are preferably used as a solution. The conjugate acid is preferably used as solvent. The particularly preferred bases NaOH and KOH are preferably used as concentrated aqueous solution. A base used as a solution preferably has a concentration of at least 25% by weight, in particular at least 40% by weight, particularly preferably about 50% by weight.

The amount of base used in step (b) can be varied within a wide range. It is possible to use from 0.01 to 5 mol of base/mol of aldehyde. Preference is given to using from 0.05 to 2 mol of base/mol of aldehyde. Particular preference is given to using from 0.1 to 1 mol of base/mol of aldehyde.

The treatment with the base is carried out in the temperature range from 100 to 250° C. The reaction is preferably carried out in the range from 110 to 220° C. The reaction is particularly preferably carried out in the range from 150 to 190° C. The duration of the treatment is determined by the temperature selected, the type and amount of base and by the desired degree of depletion for the aldehydes. The conditions are preferably selected so that the duration of the treatment is from 1 minute to 10 hours, for example from 10 minutes to 5 hours, in particular from 20 minutes to 2 hours, in particular from 30 minutes to 1.5 hours, particularly preferably from 40 minutes to 1 hour.

In a preferred embodiment, the treatment with the base is carried out at a temperature of from 160 to 185° C. for a time of from 30 to 40 minutes. The treatment is preferably carried out using 0.1 to 0.15% by weight of sodium hydroxide, based on the total composition. In a particularly preferred embodiment, the treatment with the base is carried out at a temperature of from 160 to 185° C. for a time of from 30 to 40 minutes using from 0.1 to 0.15% by weight of sodium hydroxide, based on the total composition.

According to the invention, the composition (B) comprises at least one cyclic ketone. The composition (B) usually comprises the cyclic ketone in an amount of more than 40% by weight, preferably from 50 to 99.9% by weight, in particular from 55 to 99% by weight, particularly preferably from 60 to 95% by weight.

The composition (B) can, for example, also comprise further organic compounds, for example 1,5,9-cyclododecatriene, 1,2-epoxycyclododeca-5,9-diene, cycloundecadiene carbaldehyde, $C_{12}$-diketones or traces of oligomeric compounds. The composition (B) can comprise, for example, 1,5,9-cyclododecatriene in amounts of from 0.2 to 0.6% by weight, 1,2-epoxycyclododeca-5,9-diene in amounts of from 0.01 to 0.1% by weight, cycloundecadiene carbaldehyde in amounts of from 0.5 to 1.2% by weight, $C_{12}$-diketones in amounts of from 0.5 to 3.0% by weight or traces of oligomeric compounds.

After at least part of the base has been separated off, the composition can be subjected to fill the intermediate treatments.

The cyclic olefin used in the process of the present invention preferably has at least two C—C double bonds, i.e., for example, 2, 3, 4 or 5.

In a further embodiment, the present invention therefore also provides a process as described above for preparing a cyclic ketone having from 7 to 16 carbon atoms, wherein the cyclic olefin has at least two C—C double bonds.

If the cyclic olefin has more than one C—C double bond, preference is given to only one of the C—C double bonds being oxidized in the oxidation in step (a) of the process of the invention.

According to the invention, the oxidation in step (a) is carried out so that very little backmixing, in particular ideally no backmixing, occurs in the reaction.

If only one of the C—C double bonds of the cyclic olefin comprised in composition (I) is oxidized in step (a), it is possible, for the purposes of the present invention, for the at least one remaining C—C double bond of the cyclic ketone comprised in the composition (A) or composition (B) after step (b) to be reacted in a further reaction step. For the purposes of the present invention, the at least one remaining C—C double bond is preferably hydrogenated.

According to the invention, the composition (B) obtained in step (b) is hydrogenated in step (c).

In the hydrogenation in step (c), the cyclic ketone comprised in composition (B) is hydrogenated. This gives a composition (C) comprising a cyclic ketone which preferably no longer has any C—C double bond.

In a further embodiment, the present invention therefore also provides a process as described above for preparing a cyclic ketone having from 7 to 16 carbon atoms, which additionally comprises the step (c):

(c) hydrogenation of the composition (B) in the presence of at least one catalyst to give a composition (C).

The composition (C) usually comprises the cyclic ketone in an amount of more than 80% by weight, preferably from 85 to 99.9% by weight, in particular from 88 to 99.9% by weight, particularly preferably from 90 to 99.6% by weight, more preferably from 92 to 99.0% by weight. The composition (C) usually comprises further compounds, in particular organic compounds, preferably ones having oxygen-comprising groups, for example alcohols, aldehydes or epoxides, in addition to the cyclic ketone. The organic compounds can, in particular, have the same number of carbon atoms as the cyclic ketone comprised in the composition (C).

The secondary components are, in particular, comprised in amounts of less than 20% by weight, in particular less than 15% by weight, particularly preferably less than 12% by weight, in the composition (C). For example, the secondary components are comprised in an amount of from 0.001 to 10% by weight, in particular from 0.1 to 9% by weight, preferably from 0.5 to 5% by weight, particularly preferably from 1 to 4% by weight.

According to the present invention, the composition (B) can be used directly in step (c). However, it is likewise possible for the purposes of the present invention for the composition (B) firstly to be treated and then be used in step (c).

All suitable catalysts can be used for the hydrogenation in step (c). In particular, it is possible to use at least one homogeneous catalyst or at least one heterogeneous catalyst or both at least one homogeneous catalyst and at least one heterogeneous catalyst.

The catalysts which can be used preferably comprise at least one metal of transition group 7, 8, 9, 10 or 11 of the Periodic Table of the Elements. The catalysts which can be used according to the invention more preferably comprise at least one element, selected from the group consisting of Re, Fe, Ru, Co, Rh, Ir, Ni, Pd, Pt, Cu and Au. In particular, the catalysts which can be used according to the invention comprise at least one element selected from the group consisting of Fe, Ni, Pd, Pt and Cu. The catalyst which can be used according to the invention particularly preferably comprise Pd, Pt, Ru or Ni.

Suitable homogeneous catalysts are, for example, one comprising at least one element of transition group 8, 9 or 10. Further preference is given to homogeneous catalysts comprising Ru, Rh, Ir and/or Ni. Examples which may be mentioned are $RhCl(TTP)_3$ and $Ru_4H_4(CO)_{12}$. Particular preference is given to homogeneous catalysts which comprise Ru. For example, use is made of homogeneous catalysts as described in U.S. Pat. No. 5,180,870, U.S. Pat. No. 5,321,176, U.S. Pat. No. 5,177,278, U.S. Pat. No. 3,804,914, U.S. Pat. No. 5,210,349, U.S. Pat. No. 5,128,296, US B 316,917 and in D. R. Fahey in J. Org. Chem. 38 (1973) pp. 80-87, whose relevant disclosure is fully incorporated by reference into the present patent application. Such catalysts are, for instance, $(TPP)_2(CO)_3Ru$, $[Ru(CO)_4]_3$, $(TPP)_2Ru(CO)_2Cl_2$, $(TPP)_3(CO)RuH_2$, $(TPP)_2(CO)_2RuH_2$, $(TPP)_2(CO)_2RuClH$ or $(TPP)_3(CO)RuCl_2$.

Another suitable catalyst is, in particular, at least one heterogeneous catalyst, in the case of which at least one of the abovementioned metals can be used as metal as such, as Raney catalyst and/or applied to a customary support. Preferred support materials are, for instance, activated carbons or oxides such as aluminum oxides, silicon oxides, titanium oxides or zirconium oxides. Mention may likewise be made of, inter alia, bentonites as support materials. If two or more metals are used, these can be present separately or as an alloy. Here, it is possible to use at least one metal as such and at least one other metal as Raney catalyst or at least one metal as such and at least one other metal applied to at least one support, or at least one metal as Raney catalyst and at least one other metal applied to at least one support or at least one metal as such and at least one other metal as Raney catalyst and at least one other metal applied to at least one support.

The catalysts used can, for example, also be precipitated catalysts. Such catalysts can be produced by precipitating their catalytically active components from their salt solutions, in particular from the solutions of their nitrates and/or acetates, for example by addition of solutions of alkali metal and/or alkaline earth metal hydroxides and/or carbonates, for example as sparingly soluble hydroxides, hydrated oxides, basic salts or carbonates, subsequently drying the precipitates obtained and then converting these by calcination at generally from 300 to 700° C., in particular from 400 to 600° C., into the corresponding oxides, mixed oxides and/or mixed-valence oxides which are reduced by treatment with hydrogen or hydrogen-comprising gases in the range of generally from 50 to 700° C., in particular from 100 to 400° C., to the respective metals and/or oxidic compounds having a lower oxidation state and converted into the actual catalytically active form. The reduction is generally continued until no more water is formed. In the production of precipitated catalysts which comprise a support material, the precipitation of the catalytically active components can be carried out in the presence of the respective support material. The catalytically active components can advantageously be precipitated simultaneously with the support material from the respective salt solutions.

Preference is given to using hydrogenation catalysts which comprise the metals or metal compounds which catalyze the hydrogenation deposited on a support material.

Apart from the abovementioned precipitated catalysts which comprise a support material in addition to the catalytically active components, support materials in which the catalytic hydrogenation-active component has been applied to a support material, for example by impregnation, are also generally suitable for the process of the invention.

The manner in which the catalytically active metal is applied to the support is generally not critical and the application can be effected in a variety of ways. The catalytically active metals can, for example, be applied to the support materials by impregnation with solutions or suspensions of the salts or oxides of the respective elements, drying and subsequent reduction of the metal compounds to the respective metals or compounds having a lower oxidation state by means of a reducing agent, preferably hydrogen or complex hydrides. Another possible way of applying the catalytically active metals to these supports is to impregnate the supports with solutions of salts which are easily decomposed thermally, for example nitrates or complexes which are easily decomposed thermally, for example carbonyl or hydrido complexes of the catalytically active metals, and to heat the support which has been impregnated in this way to temperatures in the range from 300 to 600° C. in order to thermally decompose the adsorbed metal compounds. This thermal decomposition is preferably carried out under a protective gas atmosphere. Suitable protective gases are, for example, nitrogen, carbon dioxide, hydrogen or the noble gases. Furthermore, the catalytically active metals can be applied to the catalyst support by vapor deposition or by flame spraying. The content of the catalytically active metals in these supported catalysts is in principle not critical for the success of the process of the invention. In general, higher contents of catalytically active metals in the supported catalysts lead to higher space-time yields than do lower contents. In general, supported catalysts whose content of catalytically active metals is in the range from 0.1 to 90% by weight, preferably in the range from 0.5 to 40% by weight, based on the total weight of the catalyst, are used. Since these content figures are based on the total catalyst including support material but the various support materials have very different specific gravities and specific surface areas, it is also conceivable that values below and above these figures can be used without this having an adverse effect on the result of the process of the invention. Of course, a plurality of catalytically active metals can also be applied to the respective support materials. Furthermore, the catalytically active metals can be applied to the support by the process of DE-A 25 19 817, EP 1 477 219 A1 or EP 0 285 420 A1. In the catalysts according to the abovementioned documents, the catalytically active metals are present as alloys which are produced by thermal treatment and/or reduction of, for example, the support material which has been impregnated with a salt or complex of the abovementioned metals.

The activation of both the precipitated catalysts and the supported catalysts can also be carried out in situ at the beginning of the reaction by means of the hydrogen present. Preference is given to activating these catalysts separately before they are used.

As support materials, it is generally possible to use the oxides of aluminum and titanium, zirconium dioxide, silicon dioxide, clay minerals such as montmorillonites, silicates such as magnesium or aluminum silicates, zeolites such as the structural types ZSM-5 or ZSM-10, or activated carbon. Preferred support materials are aluminum oxides, titanium dioxides, silicon dioxide, zirconium dioxide and activated carbon. It is of course also possible to use mixtures of various support materials as supports for catalysts which can be used in the process of the invention.

According to the invention, very particularly preferred catalysts are ones which comprise Ni, Pt and/or Pd and are applied to a support. Very preferred supports are or comprise activated carbon, aluminum oxide, titanium dioxide and/or silicon dioxide.

The at least one heterogeneous catalyst can, for example, be used as suspended catalyst and/or as fixed-bed catalyst.

If, for example, the hydrogenation in step (c) of the process of the invention is carried out using at least one suspended catalyst, the hydrogenation is preferably carried out in at least one stirred reactor or in at least one bubble column or in at least one packed bubble column or in a combination of two or more identical or different reactors.

For the present purposes, the term "different reactors" refers both to different types of reactor and to reactors of the same type which differ, for example, in terms of their geometry, for example their volume and/or their cross section and/or in terms of the hydrogenation conditions in the reactors.

If, for example, the hydrogenation in step (c) of the process of the invention is carried out using at least one fixed-bed catalyst, then preference is given to using at least one tube reactor such as at least one shaft reactor and/or one shell-and-tube reactor, with a single reactor being able to be operated in the upflow mode or the downflow mode. When two or more reactors are used, it is possible to operate at least one in the upflow mode and at least one in the downflow mode.

If, for example, a heterogeneous catalyst is used as suspended catalyst in the hydrogenation, this is, for the purposes of the present invention, preferably separated off by means of at least one filtration step. The catalyst which is separated off in this way can be recirculated to the hydrogenation or passed to at least one other desired process. It is likewise possible to work up the catalyst, for example in order to recover the metal comprise in the catalyst.

If, for example, a homogeneous catalyst is used in the hydrogenation in step (c), this is, for the purposes of the present invention, preferably separated off by means of at least one distillation step. This distillation can be carried out using one or two or more distillation columns. The catalyst which is separated off in this way can be recirculated to the hydrogenation or be passed to at least one other desired process. It is likewise possible to work up the catalyst, for example in order to recover the metal comprised in the catalyst.

Before use in any desired process, for example before recirculation to the process of the invention, both the at least one homogeneous catalyst and the at least one heterogeneous catalyst can, if necessary, be regenerated by means of at least one suitable process.

The heat can be removed from the reactor used according to the invention either internally, for example by means of cooling coils, and/or externally, for example by means of at least one heat exchanger. If, for example, at least one tube reactor is preferably used for the hydrogenation, the reaction mixture is preferably conveyed through an external circuit into which the heat removal is integrated.

If, in a preferred embodiment of the process of the invention, the hydrogenation is carried out continuously, further preference is given to using at least two reactors, more preferably at least two tube reactors, more preferably at least two tube reactors connected in series and particularly preferably precisely two tube reactors connected in series. The hydrogenation conditions in the reactors used can in each case be identical or different and are in each case in the above-described ranges.

If the hydrogenation in step (c) is carried out over at least one suspended catalyst, the residence time is generally in the range from 0.05 to 50 hours, for example in the range from 0.5 to 50 hours, preferably in the range from 1 to 30 hours and particularly preferably in the range from 1.5 to 25 hours, very particularly preferably in the range from 1.5 to 10 hours. Here, it is immaterial whether a main reactor and an after-reactor or additionally further reactors are used according to the invention. In all these embodiments, the total residence time is within the abovementioned ranges.

If the hydrogenation in the process of the invention is carried out continuously over at least one fixed-bed catalyst, the space velocity over the catalyst (kg of feed/liter of catalyst×h) is generally in the range from 0.03 to 20, preferably in the range from 0.05 to 5 and particularly preferably in the range from 0.1 to 2. It is immaterial whether a main reactor and an after-reactor or additionally further reactors are used according to the invention. In all these embodiments, the total residence time is within the abovementioned ranges.

In general, the hydrogenation temperature in the main reactor is in the range from 0 to 350° C., preferably in the range from 20 to 300° C., more preferably in the range from 50 to 250° C. and particularly preferably in the range from 80 to 220° C.

In the hydrogenation according to the invention, the hydrogen pressure in the main reactor is generally in the range from 1 to 325 bar, preferably in the range from 5 to 300 bar, more preferably in the range from 10 to 250 bar and particularly preferably in the range from 15 to 150 bar.

In the hydrogenation according to the invention in step (c), it is possible to use at least one suitable solvent or diluent. As solvents or diluents, mention may basically be made of all solvents and diluents which are not hydrogenated or reacted in another way under the hydrogenation conditions, e.g. alcohols, ethers, hydrocarbons, water, aromatics or ketones, in particular toluene or cyclododecane.

In a preferred embodiment of the process of the invention, the hydrogenation in step (c) is carried out without addition of a solvent or diluent.

In the process of the present invention, it is possible for at least one intermediate treatment to be carried out between the steps (a) and (b) or between the steps (b) and (c) or between the steps (a) and (b) and (b) and (c). For example, it is possible for unreacted starting material or by-products to be removed completely or partly in the intermediate treatment. If an intermediate treatment of the composition (A) is carried out after step (a), this gives, according to the invention, a composition (A') which is then used in step (b). It is likewise possible, according to the invention, for an intermediate treatment of the composition (B) to be carried out after step (b), which then gives, according to the invention, a composition (B') which is then used in step (c).

In a further embodiment, the present invention therefore also provides a process as described above for preparing a cyclic ketone having from 7 to 16 carbon atoms, wherein unreacted starting material or by-products are removed from the composition (A) after step (a) and before step (b) to give a composition (A').

For the purposes of the invention, it is likewise possible for an intermediate treatment to comprise a plurality of different steps which can be identical or different.

Further possible intermediate treatments are, for example:
heating of the reaction mixture;
alteration of the pressure under which the reaction mixture is. In this context, preference is given, for example, to increasing the pressure by means of, for example, at least one pump and/or at least one compressor;
introduction of at least one starting material. In particular, solvents can be introduced.
removal of product formed by means of at least one suitable measure, for example preferably by means of at least one distillation step.
removal of unreacted starting material by means of at least one suitable measure, for example preferably by means of at least one distillation step.

For the purposes of the present invention, the process of the invention can comprise further steps, for example purification steps or steps for separating off undesirable by-products, after step (c).

After step (c), it is possible to carry out, for example, a thermal treatment of the composition (C) with at least one acid or at least one catalyst comprising at least one transition metal or a further purification by means of a method selected from the group consisting of distillation, extraction and crystallization.

However, according to the invention, it is preferred that the composition (C) obtained after the hydrogenation in step (c) is not subjected to any treatment which comprises the steps
  (i) thermal treatment of the composition (C) with at least one acid or at least one catalyst comprising at least one transition metal, and
  (ii) further purification by means of a method selected from the group consisting of distillation, extraction and crystallization.

In a particular embodiment of the present invention, a purification of the composition (C) by distillation is carried out after step (c).

In a further embodiment, the present invention therefore also comprises a process as described above for preparing a cyclic ketone having from 7 to 16 carbon atoms, which comprises a purification by distillation after step (c).

In a preferred embodiment of the present invention, cyclododecatriene, preferably 1,5,9-cyclododecatriene, is used as cyclic olefin comprised in composition (I).

In a further embodiment, the present invention therefore also provides a process as described above for preparing a cyclic ketone having from 7 to 16 carbon atoms, wherein the cyclic olefin is cyclododecatriene.

If cyclododecatriene is used, preference is given, for the purposes of the present invention, to the process of the invention comprising the step (c).

Cyclododecatriene is preferably obtained by trimerization of butadiene.

In a further preferred embodiment, the present invention therefore also provides a process as described above for preparing a cyclic ketone having from 7 to 16 carbon atoms, wherein the cyclic olefin is cyclododecatriene which has been prepared from butadiene by means of trimerization.

1,5,9-Cyclododecatrienes can be prepared, for example, by trimerization of pure 1,3-butadiene, as described, for example, in T. Schiffer, G. Oenbrink, "Cyclododecatriene, Cyclooctadiene, and 4-Vinylcyclohexene", Ullmann's Encyclopedia of Industrial Chemistry, 6th Edition (2000), Electronic Release, Wiley VCH. In this process, for example, cis,trans,trans-1,5,9-cyclododecatriene, cis,cis,trans-1,5,9-cyclododecatriene and all-trans-1,5,9-cyclododecatriene are formed in the trimerization in the presence of Ziegler catalysts, as described, for example, in H. Weber et al. "Zur Bildungsweise von cis,trans,trans-cyclododecatriene-(1.5.9) mittels titanhaltiger Katalysatoren" in: Liebigs Ann. Chem. 681 (1965), pp. 10-20. Cyclododecatriene can be prepared by trimerization of 1,3-butadiene using a titanium catalyst.

While all suitable titanium catalysts can in principle be used for the trimerization, the titanium tetrachloride/ethylaluminum sesquichloride catalysts described in the article by Weber et al. is particularly suitable.

The butadiene used for the trimerization particularly preferably has a purity determined by gas chromatography of at least 99.6% and more preferably at least 99.65%. The 1,3-butadiene used particularly preferably comprises no 1,2-butadiene and no 2-butyne within the detection limits.

This trimerization generally gives mixtures comprising at least 95% by weight, preferably at least 96% by weight and more preferably at least 97% by weight of cis,trans,trans-1,5,9-cyclododecatriene. For example, the mixtures particularly preferably comprise about 98% by weight of cis,trans,trans-1,5,9-cyclododecatriene.

This mixture comprising cis,trans,trans-1,5,9-cyclododecatriene can be used as such for the reaction in step (a). It is likewise possible to separate off the cis,trans,trans-1,5,9-cyclododecatriene from the mixture by means of at least one suitable method, for example preferably by means of at least one distillation, and use it in the reaction in step (a).

For the purposes of the present invention, it is in principle possible to react any cyclododecatriene or any mixture of two or more different cyclododecatrienes with dinitrogen monoxide in step (a). Examples which may be mentioned are, inter alia, 1,5,9-cyclododecatrienes, for example, cis,trans,trans-1,5,9-cyclododecatriene or cis,cis,trans-1,5,9-cyclododecatriene or all-trans-1,5,9-cyclododecatriene.

In a very particularly preferred embodiment of the process of the invention, cis,trans,trans-1,5,9-cyclododecatriene is used as cyclododecatriene.

In a very particularly preferred embodiment of the process of the invention, an isomer mixture comprising predominantly cis,trans,trans-1,5,9-cyclododecatriene, trans,trans,trans-1,5,9-cyclododecatriene or cis,cis,trans-1,5,9-cyclododecatriene as cyclododecatriene is used. Preference is given to using an isomer mixture comprising more than 60% by weight, based on the isomer mixture, of cis,trans,trans-1,5,9-cyclododecatriene, more preferably more than 70% by weight, in particular more than 80% by weight, particularly preferably more than 90% by weight, for example more than 91% by weight, more than 92% by weight, more than 93% by weight, more than 94% by weight, more than 95% by weight, more than 96% by weight, more than 97% by weight or more than 98% by weight.

In general, the reaction according to the invention of cis,trans,trans-1,5,9-cyclododecatriene with dinitrogen monoxide in step (a) results in a cyclododeca-4,8-dienone isomer mixture comprising at least two of the isomers cis,trans-cyclododeca-4,8-dienone, trans,cis-cyclododeca-4,8-dienone and trans,trans-cyclododeca-4,8-dienone. According to the invention, preference is given to an isomer mixture in which the trans,cis isomer and cis,trans isomer are formed in approximately equal amounts and the trans,trans isomer is formed in only minor amounts compared to the other two isomers being obtained. An example of a typical isomer mixture accordingly comprises the isomers in molar ratios of about 1:1:0.08.

The reaction according to the invention of composition (I) comprising cyclododecatriene with dinitrogen monoxide in step (a) generally gives, as composition (A), a mixture comprising cyclododecadienone, preferably cyclododeca-4,8-dienone, and possibly unreacted starting material and/or possibly at least one by-product. Depending on the further use and/or work-up, the cyclododecadienone, preferably cyclododeca-4,8-dienone, can be separated off from this mixture.

The cyclododeca-4,8-dienone can be separated off from this mixture by at least one suitable method. Preference is here given to separation by distillation. The distillation here is generally carried out at a pressure in the range from 0.001 to 2 bar, preferably in the range from 0.01 to 1 bar and particularly preferably in the range from 0.02 to 0.5 bar.

In a particularly preferred embodiment of the process of the invention, a composition (B) comprising cyclododeca-4, 8-dienone is hydrogenated in step (c) to give a composition (C) comprising cyclododecanone.

In a further preferred embodiment of the invention, a composition (I) comprising cyclododecene is used in step (a). In this case, the process of the invention preferably does not comprise a step (c).

The oxidation according to the invention of the cyclododecene in step (a) generally results in a product mixture. This product mixture preferably comprises from 5 to 95% by weight, particularly preferably from 7 to 80% by weight and very particularly preferably from 10 to 75% by weight, of cyclododecanone, in each case based on the total weight of the product mixture after cooling to 20° C. and depressurization to atmospheric pressure.

The cyclododecene used as starting material, which can be used either as cis isomer or as trans isomer or as a mixture of cis and trans isomers, can in principle originate from any desired source.

For the purposes of the present invention, cyclododecene is very particularly preferably prepared by partial hydrogenation of at least one cyclododecatriene, preferably by partial hydrogenation of at least one 1,5,9-cyclododecatriene such as cis,trans,trans-1,5,9-cyclododecatriene or cis,cis,trans-1,5,9-cyclododecatriene or all-trans-1,5,9-cyclododecatriene, in particular cis,trans,trans-1,5,9-cyclododecatriene.

In a particularly preferred embodiment of the present invention, steps (a) and (b) and, if appropriate, also (c) of the process of the invention are combined with a plurality of intermediate treatment steps.

Preferred embodiments of the present invention are described by way of example below, without the process of the invention being restricted to the embodiments indicated.

In a preferred embodiment of the process of the invention, a composition (I) comprising 1,5,9-cyclododecatriene is accordingly oxidized by means of dinitrogen monoxide in step (a) to give, as composition (A), a mixture comprising unreacted cyclododecatriene together with cyclododeca-4,8-dienone as main product and dodeca-4,8,11-trienal, cycloundeca-3,7-diene carbaldehyde and cyclododecenediones as by-products.

The cyclododecatriene is separated off from this mixture, preferably by distillation, to give a mixture which consists essentially of cyclododeca-4,8-dienone together with dodeca-4,8,11-trienal, cycloundeca-3,7-diene carbaldehyde and cyclododecenediones as secondary components. The mixture is preferably depleted in dodeca-4,8,11-trienal by distillation. The cyclododecenediones are preferably then separated off, preferably by distillation, to give, as composition (A'), a mixture comprising essentially cyclododeca-4,8-dienone and cycloundeca-3,7-diene carbaldehyde with small accompanying amounts of dodeca-4,8,11-trienal.

In step (b) of the process of the invention, the resulting composition (A') is then preferably admixed with base and treated until it has been depleted in aldehydes to the desired degree. After the treatment, the base is separated off, preferably by distillation. The distillation can, for example, be carried out by means of a dividing wall column.

The composition (B) obtained in this way can then preferably be hydrogenated in step (c) to give a composition (C) which consists essentially of cyclododecanone. Step (c) can be followed by a further fine purification, for example a distillation.

In the above-described preferred embodiment, the by-products are preferably separated off from composition (A) by distillation. In a particularly preferred embodiment of the process, cyclododecatriene is distilled off overhead in a first column and a mixture comprising cyclododeca-4,8-dienone, dodeca-4,8,11-trienal, cycloundeca-3,7-diene carbaldehyde and cyclododecenediones is obtained at the bottom. In a second column, the bottom product is preferably separated into an overhead fraction which comprises essentially dodeca-4,8,11-trienal and a bottom fraction which comprises the other components. This bottom product is then preferably fractionated further in a third column to give a mixture of essentially cyclododeca-4,8-dienone and cycloundeca-3,7-diene carbaldehyde as overhead product and essentially cyclododecenediones as bottom product. The overhead product from the last column is then treated according to the invention, as composition (A'), with a base in step (b).

In a further preferred embodiment of the process, the intermediate treatment is carried out by distilling off cyclododecatriene at the top of a first column and obtaining a mixture comprising cyclododeca-4,8-dienone, dodeca-4,8,11-trienal, cycloundeca-3,7-diene carbaldehyde and cyclododecenediones at the bottom. In a second column, the bottom product is fractionated to give an overhead fraction which comprises essentially dodeca-4,8,11-trienal, a bottom fraction which comprises essentially cyclododecene-diones and a side offtake fraction which comprises essentially cyclododeca-4,8-dienone and cycloundeca-3,7-diene carbaldehyde. The side offtake fraction of the second column is then treated according to the invention, as composition (A'), with a base in step (b).

However, it is also possible according to the invention to carry out the individual steps of the intermediate treatment in a different order or not to carry out all the abovementioned separation steps.

In particular, the product obtained from step (a) can be treated directly with a base in step (b).

The invention is illustrated below by means of examples.

EXAMPLES

Example 1

1,5,9-Cyclododecatriene was oxidized by means of $N_2O$ and worked up as described in example 7 of WO 2005/030690. It was distilled so that the overhead product of the second distillation column had the following composition: cyclododeca-4,8-dienone (98% by weight), dodeca-4,8,11-trienal (0.2% by weight) and cycloundeca-3,7-diene carbaldehyde (0.7% by weight).

500 g of the overhead product were heated to 160° C. under a protective gas atmosphere ($N_2$) in a stirred flask. 5.0 g of a 25% strength aqueous NaOH solution were subsequently added by means of a syringe. The reaction mixture remained clear and homogeneous. Samples were taken at regular intervals and analyzed by GC. After 35 minutes, the solution comprised less than 20 ppm by weight of dodeca-4,8,11-trienal and only about 0.2% by weight of cycloundeca-3,7-diene carbaldehyde. After 95 minutes, the solution comprised less than 10 ppm by weight of dodeca-4,8,11-trienal and 400 ppm by weight of cycloundeca-3,7-diene carbaldehyde. In contrast, the content of cyclododeca-4,8-dienone barely changed (97% by weight).

Example 2

1,5,9-Cyclododecatriene was oxidized by means of $N_2O$ as described in example 7 of WO 2005/030690 and, as described, unreacted 1,5,9-cyclododecatriene was separated off in a first column. The bottom product from the first column had the following composition: cyclododeca-4,8-dienone (90% by weight), dodeca-4,8,11-trienal (2.2% by weight), cycloundeca-3,7-diene carbaldehyde (0.9% by weight) and cyclododecenediones (2.1% by weight). 550 g of this mixture were placed in a stirred flask and heated to 160° C. under protective gas ($N_2$). 2.75 g of a 25% strength aqueous NaOH solution were subsequently added by means of a syringe. The reaction mixture remained clear and homogeneous. Samples were taken at regular intervals and analyzed by GC. After 35 minutes, the solution comprised only about 150 ppm by weight of dodeca-4,8,11-trienal and 0.4% by weight of cycloundeca-3,7-diene carbaldehyde. After 95 minutes, the solution comprised less than 30 ppm by weight of dodeca-4,8,11-trienal and 760 ppm by weight of cycloundeca-3,7-diene carbaldehyde. The content of cyclododeca-4,8-dienone barely changed (88% by weight after 95 minutes).

In the gas chromatogram, the signals assigned to cyclododecenediones had virtually completely disappeared. New signals appeared in the chromatogram at a somewhat shorter retention time and these are assigned a molar mass of 176 g/mol.

Example 3

The mixture obtained as described in example 2 was freed of high-boiling components in a short path evaporator. About 500 g of distillate were obtained. The 500 g of the distillate were hydrogenated over 50 ml of a 5% Pd/activated carbon catalyst at about 120° C. and a hydrogen pressure of 30 bar for 5 hours in a 1 liter autoclave. The catalyst was subsequently separated off from the hydrogenation product by filtration at about 65° C. and the hydrogenation product was subsequently fractionally distilled at 10 mbar (absolute) via a 1 m packed column comprising 5 mm metal mesh rings as packing elements. 85% of the distillation feed used was obtained as cyclododecanone having a purity of 99.8%. 0.03% of cycloundecane carbaldehyde and 0.01% of dodecanol were comprised as secondary components.

The invention claimed is:

1. A process for preparing a cyclic ketone having from 7 to 16 carbon atoms which comprises at least the steps
    (a) oxidizing a composition (I) comprising at least one cyclic olefin which has from 7 to 16 carbon atoms and at least one C—C double bond by means of dinitrogen monoxide to give a composition (A),
    (b) treating the composition (A) with at least one base to give a composition (B).

2. The process according to claim 1, wherein the step (b) comprises the substeps (b1) and (b2):
    (b1) treating the composition (A) with at least one base
    (b2) removing the base.

3. The process according to claim 1, wherein the base is sodium hydroxide or potassium hydroxide.

4. The process according to claim 1, wherein the treating in step (b) is carried out at a temperature of from 100 to 250° C. for a period of from 1 minute to 10 hours.

5. The process according to claim 1, wherein the cyclic olefin has at least two C—C double bonds.

6. The process according to claim 1, which further comprises the step (c):
    (c) hydrogenating the composition (B) in the presence of at least one catalyst to give a composition (C).

7. The process according to claim 1, wherein unreacted starting material or by-products are removed from the composition (A) after step (a) and before step (b) to give a composition (A').

8. The process according to claim 6, which further comprises purifying by distillation after step (c).

9. The process according to claim 1, wherein the cyclic olefin is cyclododecatriene.

10. The process according to claim 1, wherein the cyclic olefin is cyclododecatriene which has been prepared from butadiene by means of trimerization.

11. The process according to claim 1, wherein the cyclic olefin is cyclododecene.

12. A process for preparing a cyclic ketone having from 7 to 16 carbon atoms which comprises at least the steps
    (a) oxidizing a composition (I) comprising at least one cyclic olefin which has from 7 to 16 carbon atoms and at least one C—C double bond by means of dinitrogen monoxide to give a composition (A),
    (b) treating the composition (A) with at least one base to give a composition (B),
    wherein the step (b) comprises the substeps (b1) and (b2):
    (b1) treating the composition (A) with at least one base
    (b2) removing the base.

13. The process according to claim 12, which further comprises the step (c):
    (c) hydrogenating the composition (B) in the presence of at least one catalyst to give a composition (C).

14. A process for preparing a cyclic ketone having from 7 to 16 carbon atoms which comprises at least the steps
    (a) oxidizing a composition (I) comprising at least one cyclic olefin which has from 7 to 16 carbon atoms and at least one C—C double bond by means of dinitrogen monoxide to give a composition (A),
    (b) treating the composition (A) with at least one base to give a composition (B),
    wherein the step (b) comprises the substeps (b1) and (b2):
    (b1) treating the composition (A) with at least one base and
    (b2) removing the base and
    which additionally comprises the step (c):
    (c) hydrogenating the composition (B) in the presence of at least one catalyst to give a composition (C).

15. The process according to claim 14, which further comprises purifying by distillation after step (c).

16. The process according to claim 14, wherein the cyclic olefin is cyclododecatriene which has been prepared from butadiene by means of trimerization.

* * * * *